United States Patent
Konrad

(10) Patent No.: US 7,883,724 B2
(45) Date of Patent: Feb. 8, 2011

(54) IN-VITRO DIAGNOSTIC MEDICAL DEVICES FOR DETERMINING SALIVA VOLUME

(75) Inventor: Franz Konrad, Oberndorf bei Schwanenstadt (AT)

(73) Assignee: Greiner Bio-One GmbH, Kremsmünster (AT)

( * ) Notice: Subject to any disclaimer, the term of this patent is extended or adjusted under 35 U.S.C. 154(b) by 0 days.

(21) Appl. No.: 12/220,500

(22) Filed: Jul. 25, 2008

(65) Prior Publication Data

US 2009/0017442 A1 Jan. 15, 2009

Related U.S. Application Data

(62) Division of application No. 11/134,060, filed on May 20, 2005, now abandoned.

(30) Foreign Application Priority Data

Oct. 6, 2004 (AT) .............................. A 1670/2004

(51) Int. Cl.
*A61K 35/12* (2006.01)
(52) U.S. Cl. .................................................... 424/520
(58) Field of Classification Search ........................ None
See application file for complete search history.

(56) References Cited

U.S. PATENT DOCUMENTS

| 4,093,750 | A | 6/1978 | Babayan |
| 4,820,506 | A | 4/1989 | Kleinberg et al. |
| 5,079,001 | A | 1/1992 | Affolter |
| 2003/0194374 | A1 | 10/2003 | Heasley et al. |

OTHER PUBLICATIONS

Nederfors et al. "Effects on salivary flow rate and composition of withdrawal of and re-exposure to the beta1-selective antagonist metoprolol in a hypertensive patients population", Eur J Oral Sci, 1996, 104:262-268.*

Heath et al. "Use of Buccal cells collected in mouthwash as a source of DNA for clinical testing", Arch Pathol Lab Med, 2001, 125:127-133.*

\* cited by examiner

*Primary Examiner*—Karen Cochrane Carlson
*Assistant Examiner*—Bin Shen
(74) *Attorney, Agent, or Firm*—Collard & Roe, P.C.

(57) ABSTRACT

The invention relates to a method of collecting saliva from the oral cavity for detecting a test substance, comprising the steps of (a) cleaning the oral cavity, (b) stimulating saliva secretion with a saliva-collecting solution, (c) removing the saliva-saliva collecting solution mixture from the oral cavity and collecting it in a container (1), (d) transferring the saliva-saliva collecting solution mixture into a sealable collection vessel.

12 Claims, 1 Drawing Sheet

IN-VITRO DIAGNOSTIC MEDICAL DEVICES FOR DETERMINING SALIVA VOLUME

CROSS REFERENCE TO RELATED APPLICATIONS

Applicant claims priority under 35 U.S.C. §119 of Austrian Application No. A 1670/2004 filed Oct. 6, 2004. Applicant also claims priority under 35 U.S.C. 120 because this is a Divisional Patent Application of U.S. patent application Ser. No. 11/134,060 filed May 20, 2005 now abandoned.

BACKGROUND OF THE INVENTION

1. Field of the Invention

The present invention relates to a method of collecting saliva from the oral cavity for detecting a test substance, a saliva-collecting solution for obtaining saliva, containers for biological fluids comprising a base part and a cover part, each with an external face and an internal face, the cover part having a cut-out in the form of a recess in which a transfer mechanism is disposed and incorporates a mechanism for penetrating a collection vessel provided on the external face of the cover part and a projection with two ends provided on the internal face of the cover part, a sealable collection vessel for accommodating biological fluids such as blood, for example, with an internal face directed towards a biological sample, a saliva simulation solution for imitating the composition of physiological saliva, a calibrator solution for quantifying the volume of saliva, a test kit for obtaining saliva and applications thereof.

2. Prior Art

Blood is predominantly used in both human and veterinary medicine as a means of analysing parameters of a clinically chemical nature. However, there are also other bodily fluids which provide information about the state of a patient. They differ in the way they are accessed.

The disadvantages of blood as an analysis material are its complex matrix, a limited availability, the need for qualified personnel to take samples and the time involved in this process, as well as the discomfort of the patient, accompanied by pain and stress.

Saliva is produced exclusively by three large and numerous smaller saliva glands and is predominantly generated in the oral cavity. When taking samples, it is necessary to distinguish between glandular saliva which is produced by the glands only and is taken from the relevant discharge point and mixed saliva originating in the oral cavity. Glandular saliva is primarily needed for scientific tests relating to the physiology and pathology of a specific type of gland and transport phenomena, whereas mixed saliva can predominantly be used for routine diagnostic tests which enable conclusions to be drawn about blood elements.

Saliva is a sample material that is easy to collect without causing stress and can be used for a whole series of analytical purposes. Amongst other things, saliva tests provide valuable information for diagnostic purposes and for controlling the treatment of a number of diseases. It enables proteins, hormones, metabolic metabolites, electrolytes and various pharmaceutical substances to be tested.

The use of saliva offers a number of advantages for clinical chemical diagnosis. For the patient, there are a number of different advantages to using saliva instead of blood.

The lesser discomfort to which the patient is subjected means that there is virtually no stress involved in obtaining a sample. Consequently, saliva diagnosis is of particular interest for all studies in which the hypothalamus-hypophysis-suprarenal gland axis plays a role. It is a generally known fact that repeated puncturing of the veins can mask the response of many dynamic functional tests.

Saliva diagnosis is also attractive for all tests which require frequent sampling, such as detecting biorhythms, monitoring ovulation and therapeutic treatment, for example.

In addition, there is less risk to the patient of artificial anaemia, infections and thromboses than is the case with blood samples.

Another advantage of using saliva is the lower cost of obtaining the sample because staffing costs are relatively low overall since there is no need for sampling to be done by trained doctors or nursing staff. Samples of saliva can even be taken by the patient himself and then sent to an appropriate specialist laboratory.

The use of saliva also offers a number of advantages in terms of diagnosis, such as the reflection of non-protein-bonded plasma fractions, the reflection of cellular concentration ratios, no volume pressure effect due to lipids and, in the case of some medicaments, a better correlation between the saliva concentration and the pharmacological effects.

Although saliva is produced constantly in the waking state, a total of approximately 1000 ml in 24 hours, and can be readily taken from the oral cavity, problems can also arise when collecting saliva samples, especially in the case of older patients.

Various methods and devices for taking samples of saliva are already known from the prior art.

In the simplest case, the flow of saliva is stimulated by chewing movements. Under certain conditions, however, this stimulation is not enough, for example in the case of dialysis patients and older patients, particularly in the morning after waking.

Another method is saliva collection using a Salivette®, whereby saliva is obtained by chewing on a roll of cotton wool. To obtain the saliva, the fully soaked cotton wool roll is inserted in the Salivette suspension vessel and centrifuged. The transparent saliva present is available for analysis. If solid substrates such as cotton wool are used to obtain the saliva sample, for example, it is necessary to check whether substances from whatever material was used has been adsorbed. This is of particular importance when testing for medicaments.

The flow of saliva can also be stimulated by mechanical stimulation, such as chewing movements. To this end, a piece of chewing gum or paraffin wax of a standardised size is administered and the patient is required to chew it for a certain time at a speed of 70 chewing movements/min, for example, in which case the rate of chewing movements can be monitored by means of a metronome and the saliva that has been generated in the oral cavity can be collected after 1 to 2 min.

The spitting method can also be used as a means of collecting a sample of mixed saliva. With this method, the saliva in the oral cavity is simply spat out. This procedure has to be repeated at specific time intervals.

An alternative method of obtaining saliva samples is a method whereby saliva is sucked out of the oral cavity by means of an aspirator, in which case the saliva that has collected in the oral cavity is sucked out for a predetermined period of time.

Saliva that has collected in the oral cavity can also be simply dripped out into a sample vessel.

However, the disadvantage which all of the above methods have in common is the fact that only a very small quantity of saliva can be collected from patients or, in the case of persons who have a low saliva flow, the taking of samples is not reproducible, the volume is barely quantifiable and thus gives rise to problems when it comes to using it for diagnostic purposes.

OBJECTIVE AND ADVANTAGES OF THE INVENTION

The objective of the present invention is to propose individual components and a method for taking and quantifying reproducible samples of saliva for further analysis purposes.

This objective is achieved by the invention independently in each case by a method of collecting saliva from the oral cavity with a view to detecting substances to be analysed, comprising the steps of (a) cleaning the oral cavity, (b) stimulating saliva secretion with a saliva-collecting solution, (c) removing the saliva-saliva collecting solution mixture from the oral cavity and collecting it in a container, (d) transferring the saliva-saliva collecting solution mixture to a sealable collection vessel, and is also achieved by means of a saliva-collecting solution containing a substance with taste-stimulating properties, an indicator substance and/or reagent and water, and by means of a container such that when the container is in the assembled state, the end of the projection of the transfer mechanism disposed closer to the base part is at a distance of 3 mm maximum from the base part, and by means of a sealable collection vessel whereby a solution containing a stabilising reagent or preservative and a reagent for dissolving the biological fluid and its contents, by means of a saliva imitating solution containing sodium, potassium or potassium compounds, human serum albumin, urea and water, by means of a calibrator solution of saliva-collecting solution and/or saliva imitation solution and sodium azide, potassium benzoate and/or Thimerosal®, and by means of a test kit consisting of a saliva-collecting solution and a container and the use thereof. The advantage of this approach is that adopting a standardised method and standardised components increases the reproducibility and reliability of the tests conducted on the collected saliva. By dispensing with a solid phase substrate in one of the analysis steps and because of one of the components used, it has also proved to be of advantage that none of the substances to be tested can be adsorbed. In view of the good reproducibility properties, the invention may also be used for a progress control, in which case several saliva samples are necessary. Variability from subject to subject is also lower.

The saliva-collecting solution with taste-stimulating properties increases the secretion of saliva so that a larger quantity of sample is available for analysis and fluctuations in several saliva samples are kept low.

Another advantage is that the saliva-saliva collecting solution mixture is transferred into the sealable collection vessel by means of a transfer mechanism integrated in or on the container, which means that there is no need for contact between the sample and the person conducting the test, thereby considerably reducing the risk of infection.

Since particulate elements are removed from the saliva-saliva collecting solution mixture by means of a filtration unit in the container, particles which can both affect the substances to be tested and interfere with the test itself are eliminated at an early stage.

Using a sealable collection vessel with a solution having preserving and reducing properties, on the one hand improves the stability of the saliva-saliva collecting solution mixture and on the other hand improves the elimination of various proteins, for example by centrifugation, in particular glycoproteins, which can adversely affect subsequent testing.

Calibrator solutions are advantageously used, thereby enabling the saliva volume as well as the tested substances detected in it to be quantified.

By comparing the concentration and/or extinction of the indicator sub-stances and/or reagent of the saliva-saliva collecting solution mixture with the concentration and/or extinction of the indicator substance and/or reagent present in the saliva before the sample was taken, distortion of the results of the tests due to contamination by components ingested by the patient and such like shortly before the saliva sample was taken is prevented.

The saliva-saliva collecting solution mixture contained in the evacuated collection vessel is centrifuged and optionally mixed beforehand, so that elements which might cause distortion migrate into the pellet and the clear supernatant can be used for testing in order to obtain reproducible results.

Use of the saliva-saliva collecting solution mixture for test purposes has proved to be of advantage because readily accessible sample material can be tested.

The tests can be conducted in standardised laboratory measuring equipment, obviating the need for expensive apparatus and specially trained staff to use the apparatus.

The substance with taste stimulating properties is selected from the group of inorganic and/or organic edible acids and/or salts or mixtures thereof, comprising phosphoric acid, lactic acid, citric acid, ascorbic acid, which means that the patient is not at risk of swallowing harmful saliva-collecting solution.

The substance with taste stimulating properties may also be a substance such as pilocarpin, for example, which means that medicaments that are already on the market can be used, whose compatibility has already been tested and evaluated thousands of times.

The concentration of the substance with taste stimulating properties is selected so as to be within a range with a lower limit of 0.0005%, in particular 0.01%, preferably 1%, and an upper limit of 10%, in particular 5%, preferably 2%, these selected concentrations resulting in optimum stimulation of the saliva flow without placing patients at risk.

It has proved to be of advantage if the indicator substance used contains a dye, thereby making it easier to test the saliva-saliva collecting solution mixture visually.

The dye is water-soluble, making the saliva-collecting solution simple and hence inexpensive to manufacture.

The dye preferably causes a yellow coloration and is selected from the group consisting of tartrazine, curcumin, saffron, quinoline yellow, sunset yellow FCF, yellow orange S, cochineal, carminic acid, carmine, carotene, or mixtures thereof, thereby enabling the saliva-saliva collecting solution mixture to be measured using measuring equipment which already exists in the laboratory or medical practices.

It is also possible to use a dye selected from the group consisting of riboflavin, riboflavin-5'-phosphate, chlorophyls and chlorophyllines, copper-containing complexes of chlorophyls and Chlorophyllines, caramel dye, simple sugar-based dye, sulphite lye-caramel die, ammonia-caramel dye, ammonium sulphite-caramel die, vegetable carbons, paprika extract, capsanthin, capsorubin, beetroot, betanine, anthocyans, iron oxides and hydroxides, azorubin, carmoisin, Ponceau 4R, cochineal red A, allura red AC, patent blue V, indigotin, indigo carmine, brilliant blue FCF, green S, brilliant black BN, black PN, brown HT, lycopene, Beta-apo-8'-carotinal (C 30), Beta-apo-8'-carotinic acid (C 30)-ethyl ester, lutein, substances of Maillard compounds and/or mixtures thereof, thereby enabling a plurality of different dye colours to be obtained and hence a colour coding.

The concentration of the dye is selected from a range with a lower limit of 0.0001%, in particular 0.005%, preferably 0.1%, and an upper limit of 5%, in particular 1%, preferably 0.5%, thereby keeping the cost of the dye used for the manufacture of the saliva-collecting solution very low.

If using a reagent in the sense of a medicinal product and/or in-vitro diagnostic medical devices or a pharmaceutical substance, it has proved to be of advantage to use substances which have already been tested in clinical studies and found to be harmless and which can be used to glean information about physiological and pathological states.

A reagent is advantageously admixed which can be detected with laboratory measuring equipment that is used on a routine basis, which means that tests can be conducted in every standard laboratory.

The reagent is at least one selected from a group consisting of bilirubin, acetaminophen, acid phosphatase, albumin, creatinin, alcohol, alkaline phosphatase, alaninamino-transferase, ammonia, amylase, aspaitatamino-transferase, bilirubin, unconjugated and conjugated, urea, calcium, bicarbonate, cholinesterase, LDL- or HDL cholesterine, lysozyme, amylase, creatin kinase, creatin kinase-MB, chloride, carbamazepin, creatinin, C-reactive protein, direct bilirubin, digoxin, carbon dioxide, iron, gamma-glutamyl transferase, glucose, magnetic HDL-cholesterine reagent, potassium, lactate, lactate dehydrogenase, lithium, lipase, inorganic compounds, such as for example trace elements, minerals, such as magnesium, sodium, new-born bilirubin, phenobarbital, phosphorous, phenytoin, primidon, liquor protein, salicylate, whole bilirubin, theophylline, reagents for whole iron-binding capacity, whole protein, triglyceride, urine protein, uric acid, β-microglobulin, corticosteroid- or sex hormone-binding globulin, thiocyanate, transferrin, various lipids, lipoproteins, proteins, carbohydrates, in particular water-soluble carbohydrates, vitamins, in particular water-soluble vitamins, such as for example vitamins of the B, C and F group, inorganic compounds, such as for example trace elements, minerals, hormones, such as for example aldosterone, androstenedion, cortisol, dihydroepiandrosterone, or -sulphates, oestradiol, oestriol, progesterone, testosterone, or mixtures thereof, which means that reagents that are licensed for use in the manufacture of foodstuffs can be used to manufacture the saliva-collecting solution and its effect can be classified as harmless.

The concentration of the reagent is selected so as to be within a range with a lower limit of 0.0000000001%, in particular 0.00005%, preferably 0.001%, and an upper limit of 10%, in particular 5%, preferably 2%, which means that a physiologically harmless concentration is used.

In one embodiment, a flavouring and/or flavour enhancer is added, thereby improving the taste of the saliva-collecting solution and enabling the flow of saliva to be additionally stimulated and the volume of secreted saliva increased.

The flavouring is selected from a group of sugar types and/or sugar substitutes, such as for example saccharose, maltose, fructose, and/or sweeteners such as for example saccharin, aspartam, and/or mixtures thereof, so that on the one hand persons with sugar-related illnesses will not have to forego their customary flavours and on the other hand diabetics can also gargle this saliva-collecting solution without coming to any harm and without fear of swallowing an insulin shock.

The flavouring and/or flavour enhancer may be of natural and/or synthetic origin and is selected from a group consisting of fruits, such as apple, raspberry, cherry, strawberry, lemon, orange, liquorice, herbs, quinine, caffeine, tannin, or mixtures thereof, in which case the substances used have already been processed for human consumption and will not be associated with any unpleasant sensations or taste experiences.

The concentration of flavouring and/or flavour enhancer is selected so as to be in a range with a lower limit of 0.001%, in particular 0.01%, preferably 0.1%, and an upper limit of 10%, in particular 5%, preferably 1%, thereby enabling an optimum taste to be obtained, increasing acceptance of the saliva-collecting solution.

The pH value is selected so as to be in a range of from 3, preferably 3.5, in particular 4, up to an upper limit of 6, preferably 5, in particular 4.5, thereby stimulating optimum saliva secretion, whilst also keeping the pH value low, i.e. close to the plasma pH value and thus exhibiting fewer fluctuations.

The distance of the end facing the base part is selected from a range with a lower limit of 0.1 mm, in particular 0.5 mm, preferably 1 mm, and an upper limit of 3 mm, in particular 2 mm, preferably 1.5 mm, which means that extremely low volumes can still be transferred and also a small amount of saliva-saliva collecting solution mixture whilst nevertheless enabling a high-quality test to be conducted.

In another embodiment of the container, a filtration unit is provided upstream of or in the transfer mechanism, thereby enabling the removal of particles which might distort the test.

The filtration unit is made from a material selected from a group consisting of glass wool, cotton wool, filter paper, foam rubber, regenerated cellulose, cellulose triacetate, nylon, nitrocellulose, polyvinyl difluoride (PVDF), PVP, polyether sulphonate, all of which have very good filtration properties for biological samples.

In an alternative embodiment, the filtration unit may be provided in the form of a membrane, in which case it can be integrated directly in the transfer mechanism, requiring no or minimal additional space for mounting purposes.

The filtration unit advantageously has a pore size selected so as to be within a range with a lower limit of 1 µm, in particular 10 µm, preferably 20 µm, and an upper limit of 100 µm, in particular 60 µm, preferably 50 µm, which one the one hand enables the major part of contaminant particles to be removed from the saliva-saliva collecting solution mixture and, on the other hand ensures permeability without any risk of clogging.

The stabilising or preserving reagent may be potassium benzoate, potassium sorbate, sodium azide and/or Thimerosal®, in which case the saliva-saliva collecting solution mixture can be stored for longer periods without the shelf life of the substances to be tested being placed at risk due to the effect of bacteria or enzymes.

The concentration of potassium benzoate or potassium sorbate is selected so as to be within a range with a lower limit of 0.05%, in particular 0.1%, preferably 1%, and an upper limit of 10%, in particular 5%, preferably 2%, and the concentration of sodium azide or Thimerosal® is selected so as to be within a range with a lower limit of 0.005%, in particular 0.01%, preferably 0.1%, and an upper limit of 1%, in particular 0.5%, preferably 0.2%, which produces the best effect for the desired effects, namely stabilisation and preservation.

The reagent used for dissolution purposes is ammonium sulphate, sodium, potassium and/or calcium chloride, thereby resulting in changes in the surface properties of proteins, for example, in particular glycoproteins and proteoglycans, enabling these proteins to be eliminated so that they can not distort the subsequent tests.

The concentration of the reagent used for dissolution purposes is selected so as to be within a range with a lower limit of 0.005%, in particular 0.01%, preferably 0.1%, and an upper limit of 5%, in particular 1%, preferably 0.5%, so that although reducing effects occur, the substances to be tested are not altered, which could otherwise distort the test.

The volume of the solution is selected so as to be within a range with a lower limit of 5 μl, in particular 20 μl, preferably 30 μl, and an upper limit of 500 μl, in particular 100 μl, preferably 50 μl, thereby enabling an optimum coating of the internal face of a 9.5 ml collection vessel to be obtained.

In another embodiment, the internal face of the collection vessel is sprayed with the solution and optionally dried, thereby ensuring that the whole volume remains unaltered and an error-free quantification of the quantity of saliva is possible.

It has also proved to be of advantage if the collection vessel is evacuated because this enables the saliva-saliva collecting solution mixture to be transferred from the container and into the collection vessel automatically, thereby avoiding any danger to the person taking the sample or conducting the test.

The concentration of sodium, potassium or calcium compounds in the saliva-imitating solution is selected so as to be in a range with a lower limit of 0.001%, in particular 0.01%, preferably 0.1%, and an upper limit of 20%, in particular 10%, preferably 5%, that of human serum albumin is selected so as to be within a range with a lower limit of 0.001%, in particular 0.01%, preferably 0.1%, and an upper limit of 5%, in particular 2.5%, preferably 1%, and that of urea is selected so as to be within a range with a lower limit of 0.0005%, in particular 0.001%, preferably 0.01%, and an upper limit of 2%, in particular 1%, preferably 0.5%, so that physiological concentrations of saliva can be imitated, thereby making a comparison with native saliva possible.

In one embodiment, lactoferrin is added in a concentration selected so as to be within a range with a lower limit of 0.000001%, in particular 0.00001%, preferably 0.0001%, and an upper limit of 0.1%, in particular 0.01%, preferably 0.005%, in order to enable another component which is present in native saliva to be detected, thereby increasing reproducibility.

Gelatine may also be added in a concentration selected from a range with a lower limit of 0.005%, in particular 0.01%, preferably 0.1%, and an upper limit of 5%, in particular 1%, preferably 0.5%, thereby also imitating the native composition of saliva.

The pH value of the saliva-imitation solution is selected so as to be within a range with a lower limit of 5, preferably 5.5, in particular 6, and an upper limit of 7.5, preferably 7, in particular 6.5, thereby optimising the quantification process.

The saliva-collecting solution and the saliva imitation solution are contained in the calibrator solution in an approximately inversely proportional ratio, thereby enabling quantification.

The volume of the saliva-collecting solution and the saliva imitation solution may respectively be kept within a gradient, thereby enabling quantification.

The concentration of sodium azide, potassium benzoate, potassium sorbate and/or Thimerosal® is selected so as to be in a range with a lower limit of 0.005%, in particular 0.01%, preferably 0.1%, and an upper limit of 5%, in particular 1%, preferably 0.5%, thereby enabling the shelf life of the solution to be lengthened.

The test kit advantageously contains a saliva-collecting solution and a container, which means that the saliva sample can be taken from the patient without the need for qualified medical personnel.

As a result of the sealable collection vessel in the test kit, the sample can be sent through the mail.

The saliva imitation solution and/or at least one calibrator solution in the test kit enable the volume of saliva to be quantified.

In one embodiment of the test kit, at least one microtitre plate, a test tube and/or instructions for use are included, which means on the one hand that standardised laboratory measuring equipment can be used for evaluation purposes and on the other hand quantification can also be conducted by untrained personnel.

MORE DETAILED DESCRIPTION OF PREFERRED EMBODIMENTS

Figure 1:
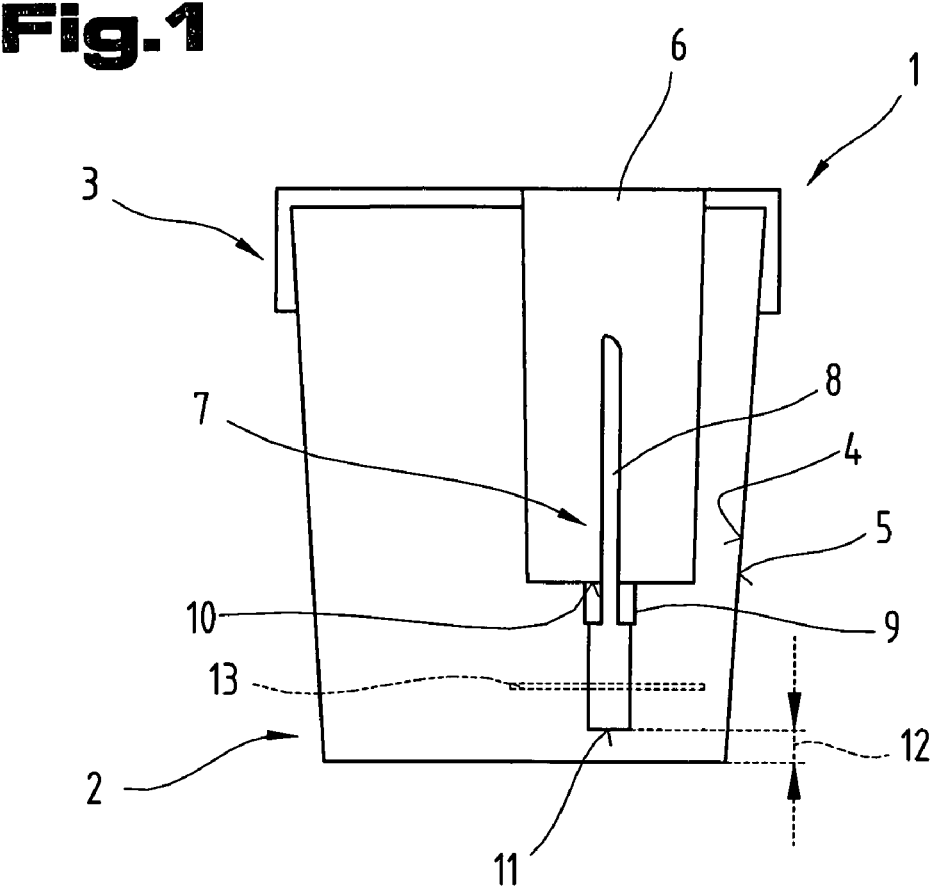
FIG. 1 shows a cross-section through a container.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

The present invention discloses a method of collecting and quantifying saliva or its volume. Also disclosed are the individual components needed for this purpose.

The individual components of the saliva-collecting system will be described below and it should be pointed out that each component constitutes an invention in its own right.

The saliva-collecting solution consists of at least one taste stimulant, an indicator substance and/or reagent and water. The purpose of the taste stimulant is to stimulate saliva secretion. The taste stimulant is selected from inorganic and/or organic edible acids and/or salts or mixtures thereof. Organic edible acids which may be used include, for example, ascorbic acid, lactic acid, etc. Citric acid is used by preference. Alternatively or in addition to organic and/or inorganic edible acids, such as phosphoric acid for example, an active substance such as pilocarpin, for example, can be used to stimulate saliva secretion. Salts of the inorganic and organic edible acids listed above may also be used, such as sodium or potassium salts, for example.

The concentration of the substance with taste-stimulating properties may be selected from a range with a lower limit of 0.0005%, in particular 0.01%, preferably 1%, and an upper limit of 10%, in particular 5%, preferably 2%.

The saliva-collecting solution also contains an indicator substance and/or reagent and the indicator substance is preferably a dye. All dyes which are covered by directive 94/36/EG in its current version may be considered. In a preferred embodiment, the dye used is one which is water-soluble and causes a yellow colouration. Dyes which result in yellow colouration include tartrazine, curcumin, saffron, quinoline yellow, sunset yellow FCF, yellow orange S, cochineal, carminic acid, carmine, carotene, and mixtures thereof.

Naturally, other dyes which cause a different colouration of the saliva-collecting solution may also be used, such as for example riboflavin, riboflavin-5'-phosphate, chlorophyls and chlorophyllines, copper-containing complexes of chlorophyls and chlorophyllines, caramel dye, simple sugar-based dye, sulphite lyes-sugar-based dye, ammonia-caramel dye, ammonium sulphite-caramel dye, vegetable carbons, paprika extract, capsanthin, capsorubin, beetroot, betanin, antho-cyans, iron oxides and hydroxides, azorubin, carmoisin, Ponceau 4R, cochineal red A, allura red AC, patent blue V, indigotin, indigo carmine, brilliant blue FCF, green S, brilliant black BN, black PN, brown HT, lycopene, beta-apo-8'-carotinal (C 30), beta-apo-8'-carotinic acid (C 30)-ethyl ester, lutein, sub-stances of Maillard compounds and/or mixtures thereof.

The concentration of the dye is selected so as to be in a range with a lower limit of 0.0001%, in particular 0.005%, preferably 0.1%, and an upper limit of 5%, in particular 1%, preferably 0.5%, thereby producing a colouration of the saliva-collecting solution which can be detected by photometric means, for example.

Irrespective of the concentration of dye used in the saliva-collecting solution, extinction of the saliva-collecting solution can be determined at a pre-defined wavelength.

As an alternative to the indicator substance or in addition to it, a reagent can be admixed with the saliva-collecting solution.

Reagents which might be used include those within the meaning of a medicinal product (in accordance with directive 93/42/EEC in its current version), in-vitro diagnostic medical devices (in accordance with directive 98/79/EC in its current version) and/or pharmaceutical substances, in particular those which have already been evaluated as being harmless in clinical trials. The reagent might also be substances conforming to directive 95/2/EC which are not defined as dyes or sweetening reagents but whose use is permitted in foodstuffs.

Reagents which might be considered include bilirubin, acetaminophen, acid phosphatase, albumin, creatinin, alcohol, alkaline phosphatase, alaninamino-transferase, ammonia, amylase, aspartatamino-transferase, bilirubin, unconjugated and conjugated, urea, calcium, bicarbonate, cholinesterase, LDL or HDL cholesterine, lysozyme, amylase, creatin kinase, creatin kinase-MB, chloride, carbamazepin, creatinin, C-reactive protein, direct bilirubin, digoxin, carbon dioxide, iron, gamma-glutamyl transferase, glucose, magnetic HDL-cholesterine reagent, potassium, lactate, lactate dehydrogenase, lithium, lipase, inorganic compounds, such as for example trace elements, minerals, such as for example magnesium, sodium, new-born bilirubin, phenobarbital, phosphorous, phenytoin, primidon, liquor protein, salicylate, whole bilirubin, theophylline, reagent for whole iron-bonding capacity, whole protein, triglyceride, urine protein, uric acid, β-microglobulin, corticosteroid or sexual hormone bonding globulin, thiocyanate, transferrin, various lipids, lipoproteins, proteins, carbohydrates, in particular water-soluble carbohydrates, vitamins, in particular water-soluble, such as for example vitamins from the B, C and F group, inorganic compounds such as for example trace elements, minerals, hormones, such as for example aldosterone, androstenedion, cortisol, dihydroepiandrosterone, or -sulphates, oestradiol, oestriol, progesterone, testosterone, or mixtures thereof.

The concentration of the reagent is selected so as to be within a range with a lower limit of 0.0000000001%, in particular 0.00005%, preferably 0.001%, and an upper limit of 10%, in particular 5%, preferably 2%.

In one embodiment of the saliva-collecting solution, a flavouring and/or flavour enhancer may be added, which enhances the citric acid flavour, for example, or sweetens the saliva-collecting solution, in which case, this may be achieved by adding different types of sugar or sugar substitutes, for example, such as saccharose, maltose, fructose, and/or sweeteners such as saccharin, aspartam, and/or mixtures thereof. All sub-stances which fall within the scope of the current version of directive 94/35/EC may be used as sweeteners.

In order to improve the flavour of the saliva-collecting solution, flavourings and/or flavour enhancers of both natural and synthetic origin may be used in order to imitate the taste of apple, raspberry, cherry, strawberry, lemon, lime, orange, liquorice, herbs, quinine, caffeine, tannin, or mixtures thereof.

The concentration of flavouring and/or flavour enhancer is selected so as to be within a range with a lower limit of 0.001%, in particular 0.01%, preferably 0.1%, and an upper limit of 10%, in particular 5%, preferably 1%.

The pH value of the saliva-collecting solution is selected so as to be within a range with a lower limit of 3, preferably 3.5, in particular 4 and an upper limit of 6, preferably 5, in particular 4.5.

To avoid contamination, the saliva-collecting solution is sterilised using methods known from the prior art, such as for example sterile filtering or autoclaving, after which it can then be split up into individual quantities. The saliva-collecting solution is poured into unbreakable vessels and sealed so as to be air-tight. It is of advantage to store the saliva-collecting solution protected from light.

The volume of the saliva-collecting solution used for rinsing the oral cavity is selected so as to be within a range with a lower limit of 0.5 ml, preferably 1 ml, in particular 2 ml and an upper limit of 10 ml, preferably 7 ml, in particular 5 ml. A volume of 4 ml of the saliva-collecting solution has proved to be of particular advantage for rinsing the oral cavity. The oral cavity can naturally be rinsed with the saliva-collecting solution several times. Prior to rinsing the oral cavity with the saliva-collecting solution, the mucous membrane of the oral cavity is cleaned, for example by gargling water. It is also of advantage to wait for a period of about 30 to 60 min. before rinsing the oral cavity with the saliva-collecting solution. No food and also no liquid should be taken, in order to prevent any distortions to the test. In order to rule out such distortions, another option is to determine the concentration of indicator substance or reagent present before taking the saliva from the oral cavity of the patient and to make allowance for it in the subsequent test by applying a correction factor, for example.

The saliva-collecting solution is left in the oral cavity for a period selected from a range with a lower limit of 20 sec, preferably 30 sec, in particular 45 sec, and an upper limit of 10 min, preferably 4 min, in particular 3 min. It is of particular advantage to leave the saliva-collecting solution in the oral cavity for a period of 1 to 2 min.

The resultant mixture of saliva and saliva-collecting solution or an aliquot of it can be used directly for tests or it can be centrifuged and the supernatant can be examined by methods of the wet-chemical or immunological analysis type, known from the prior art.

The saliva-saliva collecting solution mixture is preferably collected in a container 1 and further processed and quantification of the volume or analysis will not take place until later.

Several examples of the composition of the saliva-collecting solution are listed below, although it should be pointed out at this stage that the saliva-collecting solution proposed by the invention is not limited to the examples below.

| | |
|---|---|
| Potassium hydrogen citrate | 5 g |
| Potassium citrate tribasic monocitrate | 1 g |
| Quinoline yellow | 50 mg |
| Top up with distilled water to a volume of 1000 ml | |
| Adjust to a pH value of 3.5 | |
| Sodium dihydrogen citrate | 12 g |
| Sodium citrate tribasic monocitrate | 6 g |
| Tartrazine | 30 mg |
| Top up with distilled water to a volume of 1000 ml | |
| Adjust to a pH value of 5.2 | |
| Sodium dihydrogen citrate | 20 g |
| Sodium citrate tribasic monocitrate | 8 g |
| Glucose | 5 g |
| Top up with distilled water to a volume of 1000 ml | |
| Adjust to a pH value of 4.0 | |
| Sodium dihydrogen citrate | 7 g |
| Sodium citrate tribasic monocitrate | 2 g |
| Tartrazine | 50 mg |
| Top up with distilled water to a volume of 1000 ml | |
| Adjust to a pH value of 4.2 | |
| Ascorbic acid | 4 g |
| Curcumin | 2 g |
| Top up with distilled water to a volume of 1000 ml | |
| Adjust to a pH value of 5 | |
| Pilocarpin | 6 mg |
| Yellow orange S | 200 mg |
| Cholesterine | 100 mg |
| Strawberry flavouring | 10 mg |
| Top up with distilled water to a volume 1000 ml | |
| Adjust to a pH value of 4.5 | |

As an alternative to sodium dihydrogen citrate and sodium citrate tribasic monocitrate respectively, it would also be possible to use their potassium or calcium compounds.

In an alternative embodiment, the quantity of dye added is set by determining the optical density (extinction) of the saliva-collecting solution. In respect of extinction, it is desirable to aim for a target of 2 and this target value is obtained by adding an appropriate quantity of the desired dye, for example tartrazine. The target value for the optical density of the saliva-collecting solution is selected so as to be within a range with a lower limit of 1.0, preferably 1.2, in particular 1.5 and an upper limit of 2.8, preferably 2.6, in particular 2.4.

The concentration of tartrazine in the saliva-collecting solution is selected from a range with a lower limit of 1 mg/l, preferably 10 mg/l, in particular 50 mg/l and an upper limit of 500 mg/l, in particular 250 mg/l, preferably 100 mg/l. It is of particular advantage to use tartrazine in a concentration of 50 mg/l.

In order to determine the optical density (OD), synonymous with extinction, a wavelength may be used which is selected from a range with a lower limit of 380 nm, preferably 400 nm, in particular 420 nm and an upper limit of 800 nm, preferably 680 nm, in particular 560 nm. The optical density of the saliva-collecting solution with tartrazine is preferably determined at a wavelength of 450 nm.

As already explained in the examples given above, in one alternative embodiment of the saliva-collecting solution, instead of or in addition to the dye, a reagent may be added, such as glucose for example. The concentration of glucose in the saliva-collecting solution is selected from a range with a lower limit of 1 g/l, preferably 2 g/l, in particular 3 g/l and an upper limit of 12 g/l, preferably 10 g/l, in particular 8 g/l. It is of particular advantage to use a concentration of 4 g/l of glucose in the saliva-collecting solution.

Depending on what indicator substance and/or reagent is used in the composition of the saliva-collecting solution, it may fall under the category of both medicinal product or pharmaceutical product are also foodstuffs.

The invention relating to the container 1 will be explained in more detail with reference to FIG. 1 of the appended drawings.

The container 1 in FIG. 1 consists of a base part 2 and a cover part 3, each with an internal 4 and external face 5, the base part 2 being an approximately cylindrical beaker.

The base part 2 is preferably made from plastic, in particular polypropylene. Naturally, the base part 2 may also be made from other materials, such as polystyrene, polyethylene.

The cover part 3 is also made from plastic, preferably from polyethylene, and may be coloured or made from coloured plastic.

Also disposed in the cover part 3 is a cut-out 6, forming a recess, in which a transfer mechanism 7 is disposed, comprising a device for penetrating 8 a collection vessel on the external face 5 of the cover part 3 and an approximately tubular projection 9 with two ends, the top end 10 and the bottom end 11, on the internal face 4 of the cover part 3. The penetration device 8, which might be a needle for example, is disposed on the side of the transfer mechanism 7 directed towards the external face 5 of the cover part 3. Disposed on the side directed towards the internal face 4 of the container 1 is the approximately tubular projection 9 in the form of a cylindrical tube. Between the tubular projection 9, which is preferably also made from plastic, in particular polypropylene, and the penetration device 8 is a thread or plug-in connection, which can be fixed in the cut-out 6 of the cover part 3. Containers of the type described above 1 comprising a base and a cover part are known from the prior art, such as those made by the company, Greiner Bio-One, the Vacuette®-urine beaker.

In the embodiment of the container 1 proposed by the invention, the distance 12 between the bottom end 11 of the tubular projection 9 and the base of the internal face 4 of the base part 2 is selected so as to be within a range with a lower limit of 0.1 mm, in particular 0.5 mm, preferably 1 mm, and an upper limit of 3 mm, in particular 2 mm, preferably 1.5 mm. It has proved to be of particular advantage to opt for a distance 12 of 1 mm. The short distance 12 between the bottom end 11 of the tubular projection 9 and the base of the base part 2 of the container 1 is primarily used as a means of also enabling small quantities or residual volumes of a biological fluid, such as urine, saliva-saliva collecting solution mixture, etc., for example, to be removed from the container 1 via the tubular projection 9. Since some infectious test substances are also tested when analysing saliva, one advantage of using the container 1 proposed by the invention is that the sample can be transferred directly into a new vessel without having to be removed from the container by a person.

In one embodiment of the container 1, a filtration unit 13 is provided. This filtration unit 13 is disposed in the region of the integrated transfer mechanism 7 and can be positioned between the penetration device 8 and the tubular projection 9 of the transfer mechanism 7, for example. In an alternative embodiment, the filtration unit 13 is connected upstream of the tubular projection 9 or within the contour of the tubular projection 9. Particulate elements are filtered out of the saliva-saliva collecting solution mixture by the filtration unit 13.

The filtration unit 13 may be made from various materials, such as glass wool, cotton wool, filter paper, foam rubber, regenerated cellulose, cellulose triacetate, nylon, nitrocellulose, polyvinyl difluoride (PVDF), PVP, polyether sulphonate, for example. In a preferred embodiment, the filtration unit 13 is made from cellulose triacetate.

In another embodiment of the filtration unit 13, the latter is provided in the form of a membrane in the region of the transfer mechanism 7, in particular between the penetration device 8 and the tubular projection 9.

The pore size of the filtration unit 13 is selected so as to be within a range with a lower limit of 1 µm, in particular 10 µm, preferably 20 µm, and an upper limit of 100 µm, in particular 60 µm, preferably 50 µm. A pore size of 30 µm to 40 µm has proved to be of particular advantage.

By means of the penetration device, the saliva-saliva collecting solution mixture can be transferred into a new vessel. An evacuated collection vessel known from the prior art is suitable for this purpose. Evacuated collection vessels are made by the company, Greiner Bio-One, for example, under the name of Vacuette® or by the Becton Dickinson company under the name of Vacutainer®. By using an evacuated vessel, the saliva-saliva collecting solution mixture is automatically transferred from the container 1 into the collection vessel.

The collection vessel proposed by the invention contains a solution containing reagents, which have the properties of stabilising and preserving the solution, such as potassium benzoate, sodium azide and/or Thimerosal®, and also reagents which enable dissolution, such as ammonium sulphate, sodium chloride and/or potassium chloride, for example. This causes a reduction in the hydrate skin and hence a change in the surface properties of a protein, in particular a glyco-protein or proteoglycan. Unwanted proteins can therefore be eliminated during the centrifugation step, whereas other substances which have to be detected during subsequent testing remain in the supernatant.

The concentration of potassium benzoate is selected so as to be within a range with a lower limit of 0.05%, in particular 0.1%, preferably 1%, and an upper limit of 10%, in particular 5%, preferably 2%, that of sodium azide or Thimerosal® is selected so as to be within a range with a lower limit of 0.005%, in particular 0.01%, preferably 0.1%, and an upper limit of 1%, in particular 0.5%, preferably 0.2%, and that of the reagent used for dissolution purposes is selected so as to be in a range with a lower limit of 0.005%, in particular 0.01%, preferably 0.1%, and an upper limit of 5%, in particular 1%, preferably 0.5%.

Possible compositions of the solution contained in the collection vessel are listed below, although this list should not be construed as restricting the invention in any way.

| | |
|---|---|
| Potassium benzoate | 1 g/l |
| Potassium chloride | 0.05 g/l |
| Potassium benzoate | 8 g/l |
| Sodium chloride | 15 g/l |
| Thimerosal ® | 0.05 g/l |
| Ammonium sulphate | 0.5 g/l |
| Sodium azide | 0.5 g/l |
| Ammonium sulphate | 1.5 g/l |
| Potassium sorbate | 0.8 g/l |
| Ammonium sulphate | 1.2 g/l |
| Sodium azide | 0.01 g/l |
| Potassium chloride | 0.015 g/l |
| Sodium chloride | 3 g/l |

The internal face of an evacuated collection vessel is preferably sprayed with the solution containing a selection of the components listed above, on the one hand in order to obtain a uniform coating of the internal face of the collection vessel and on the other hand to ensure that the volume and hence the concentration of the reagents contained in it do not change.

In a preferred embodiment, the internal face of the evacuated collection vessel is sprayed with a mixture of a solution containing sodium acite in a concentration of 0.5 µl and ammonium sulphate in a concentration of 1.5 g/l.

For spraying the internal face of the evacuated collection vessel with a capacity of approximately 10 ml, a volume of solution is selected from a range with a lower limit of 5 µl, preferably 10 µl, in particular 20 µl and an upper limit of 100 µl, preferably 80 µl, in particular 50 µl. A volume of 30 µl has proved to be of particular advantage. Naturally, if a collection vessel with a smaller or bigger capacity is used, the quantity is also reduced or increased accordingly.

In another embodiment, when the internal face of the collection vessel has been sprayed with the solution, it may also be dried.

Alternatively, the collection vessel may also be filled with solution in the dry state in order to avoid affecting the volume of fluids contained in it.

Naturally, it would also be possible for the person skilled in this field to use other reagents which also make it easier to centrifuge off cellular elements, in particular glycoproteins, so that the surface properties are modified, and which can be used for preservation or stabilisation purposes.

Such evacuated vessels proposed by the invention are preferably used for transferring the saliva-saliva collecting solution mixture from the container 1.

The evacuated collection vessel with the saliva-saliva collecting solution mixture contained in it is tilted, shaken and/or vortexed prior to centrifugation, in order to ensure thorough mixing of the saliva-saliva collecting solution mixture with the reagents on the internal face of the evacuated collection vessel. The saliva-saliva collecting solution mixture is centrifuged in the evacuated collection vessel for approximately 10 min at approximately 1,800 g. The centrifugation is selected so that particulate elements migrate into the pellet during centrifugation. The supernatant is used for further testing. A plurality of different test substances from the supernatant can be analysed.

The supernatant of the evacuated collection vessel may also be photometrically measured in the collection vessel immediately after centrifugation or alternatively the supernatant can be transferred into a new vessel, for example a test tube or micro-titre plate.

Prepared in this manner, the supernatant can now be used for further subsequent tests, for example based on clinical chemistry or for lateral flow immunoassays.

The saliva imitation solution proposed by the invention is used to conduct a quantification of the saliva volume. The saliva imitation solution is a protein-containing solution, which may also be termed a synthetic or artificial saliva. It consists of at least sodium, potassium or calcium compounds, human serum albumin, urea and water.

The concentration of the sodium, potassium or calcium compounds is selected so as to be within a range with a lower limit of 0.001%, in particular 0.01%, preferably 0.1%, and an upper limit of 20%, in particular 10%, preferably 5%, that of human serum albumin is selected from a range with a lower limit of 0.001%, in particular 0.01%, preferably 0.1%, and an upper limit of 5%, in particular 2.5%, preferably 1%, and that of urea is selected from a range with a lower limit of 0.0005%, in particular 0.001%, preferably 0.01%, and an upper limit of 2%, in particular 1%, preferably 0.5%.

Another embodiment of the saliva imitation solution contains lactoferrin and/or gelatine in order to provide as accurate an imitation of native saliva as possible. In order to dissolve the gelatine, the saliva imitation solution is heated, for example to 40° C.

The concentration of lactoferrin is selected so as to be within a range with a lower limit of 0.000001%, in particular 0.00001%, preferably 0.0001%, and an upper limit of 0.1%, in particular 0.01%, preferably 0.005%, and the concentration of gelatine is selected so as to be within a range with a lower limit of 0.005%, in particular 0.01%, preferably 0.1%, and an upper limit of 5%, in particular 1%, preferably 0.5%.

The pH value of the saliva imitation solution is a value with a lower limit of 5, preferably 5.5, in particular 6 and an upper limit of 7.5, preferably 7, in particular 6.5.

The solution is sterilised using methods known from the prior art, such as sterile filtration for example, and then split into individual portions.

Possible compositions of the saliva imitation solution may be taken from the embodiments given as examples below, although it should be pointed out that this list should not be construed as limiting the saliva imitation solution proposed by the invention.

| | |
|---|---|
| $NaHCO_3$ | 0.4 g |
| NaCl | 0.04 g |
| $K_2CO_3$ | 0.01 g |
| Human serum albumin | 20 mg |
| Urea | 10 mg |
| Top up with distilled water to 1000 ml | |
| Adjust pH value to 7.5 | |

| | |
|---|---|
| $KHCO_3$ | 50 g |
| KCl | 5 g |
| $Na_2CO_3$ | 3 g |
| Human serum albumin | 2 g |
| Urea | 1 g |
| Top up with distilled water to 1000 ml | |
| Adjust pH value to 5 | |

| | |
|---|---|
| $NaHCO_3$ | 10 g |
| $CaCl_2$ | 1 g |
| $K_2CO_3$ | 0.1 g |
| Human serum albumin | 750 mg |
| Urea | 500 mg |
| Gelatine | 1 g |
| Top up with distilled water to 1000 ml | |
| Adjust pH value to 5.5 | |

| | |
|---|---|
| $NaHCO_3$ | 2 g |
| NaCl | 5 g |
| $K_2CO_3$ | 2 g |
| Human serum albumin | 2 g |
| Urea | 1 g |
| Lactoferrin | 1 g |
| Top up with distilled water to 1000 ml | |
| Adjust pH value to 7 | |

| | |
|---|---|
| $NaHCO_3$ | 0.002 g |
| NaCl | 0.03 g |
| $K_2CO_3$ | 0.08 g |
| Human serum albumin | 50 mg |
| Urea | 50 mg |
| Lactoferrin | 0.1 mg |
| Gelatine | 100 mg |
| Top up with distilled water to 1000 ml | |
| Adjust pH value to 6.8 | |

| | |
|---|---|
| $NaHCO_3$ | 4.2 g |
| NaCl | 0.5 g |
| $K_2CO_3$ | 0.2 g |
| Human serum albumin | 250 mg |
| Urea | 150 mg |
| Lactoferrin | 0.1 g |
| Gelatine | 500 mg |
| Top up with distilled water to 1000 ml | |
| Adjust pH value to 6.5 | |

In another embodiment of the present invention, the imitation solution can be used to produce at least one calibrator solution.

The calibrator solution contains at least saliva-collecting solution and/or a saliva imitation solution and sodium azide, potassium benzoate, potassium sorbate and/or Thimerosal®.

The calibrator solution preferably consists of a dilution sequence of the saliva imitation solution and saliva-collecting solution, in which case the two solutions are present in an approximately inversely proportional ratio. The dilution sequence may be prepared in a concentration gradient of x(n+1), where x represents the number of ml of the respective solution used and n is a whole natural number.

In one possible embodiment, the dilution sequence comprises the dilution sequence of five different concentrations of the saliva imitation solution and saliva-collecting solution.

The concentration of sodium azide, potassium benzoate, potassium sorbate and/or Thimerosal® is selected so as to be within a range with a lower limit of 0.005%, in particular 0.01%, preferably 0.1%, and an upper limit of 5%, in particular 1%, preferably 0.5%.

A person skilled in this field would naturally also be able to use more or less than five calibrator solutions and vary the ratio of saliva imitation solution and saliva-collecting solution relative to one another for the dilution sequence to enable the saliva volume to be quantified.

Examples of compositions are listed below in order to illustrate the described calibrator solutions, although these should not be construed as restricting the invention in any way

| | Calibrator solution 1 | Calibrator solution 2 | Calibrator solution 3 | Calibrator solution 4 | Calibrator solution 5 |
|---|---|---|---|---|---|
| Saliva-collecting solution | 99.95% | 74.95% | 49.975% | 25% | 0% |
| Saliva-imitation solution | 0% | 25% | 49.975% | 74.95% | 99.95% |
| Sodium azide | 0.05% | 0.05% | 0.05% | 0.05% | 0.05% |
| Saliva-collecting solution | 99.95% | 89.95% | 79.95% | 69.95% | 59.95% |
| Saliva-imitation solution | 0% | 10% | 20% | 30% | 40% |
| Thimerosal ® | 0.05% | 0.05% | 0.05% | 0.05% | 0.05% |

| | Calibrator solution 6 | Calibrator solution 7 | Calibrator solution 8 | Calibrator solution 9 | Calibrator solution 10 | Calibrator solution 11 |
|---|---|---|---|---|---|---|
| Saliva-collecting solution | 49.975% | 40% | 30% | 20% | 10% | 0% |
| Saliva-imitation solution | 49.975% | 59.95% | 69.95% | 79.95% | 89.95% | 99.95% |
| Thimerosal ® | 0.05% | 0.05% | 0.05% | 0.05% | 0.05% | 0.05% |

|  | Calibrator solution 1 | Calibrator solution 2 | Calibrator solution 3 | Calibrator solution 4 |  |
| --- | --- | --- | --- | --- | --- |
| Saliva-collecting solution | 99.5% | 66.65% | 33.3% | 0% |  |
| Saliva-imitation solution | 0% | 33.3% | 66.65% | 99.5% |  |
| Potassium benzoate | 0.5% | 0.5% | 0.5% | 0.5% |  |

|  | Calibrator solution 1 | Calibrator solution 2 | Calibrator solution 3 | Calibrator solution 4 | Calibrator solution 5 |
| --- | --- | --- | --- | --- | --- |
| Saliva-collecting solution | 99.995% | 74.995% | 49.9975% | 25% | 0% |
| Saliva-imitation solution | 0% | 25% | 49.9975% | 74.995% | 99.995% |
| Sodium azide | 0.005% | 0.005% | 0.005% | 0.005% | 0.005% |

Specifying the exact volume of the saliva obtained is of major importance because it subsequently enables a calculation to be made as to what quantity of the sub-stances to be tested was contained in the biological sample originally taken.

By using different indicator substances, in particular dyes or reagents, the calibrator solutions may also be made up in different compositions accordingly. By way of example, in addition to a saliva-collecting solution incorporating dye, others containing glucose may be used as calibrator solutions.

Instead of the described saliva imitation solution, distilled water may also be used to make the calibrator solution or dilution sequences of it. However, the saliva imitation solution is preferred as a means of making the saliva volume more easily quantifiable.

To prevent contamination, the calibrator solutions are sterilised using methods known from the prior art.

In one embodiment, at least some of the components mentioned above are combined to make up a test kit. The test kit contains at least the saliva-collecting solution and a container 1 for accommodating the saliva-saliva collecting solution mixture. The test kit may be completed by a sealable collection vessel, saliva imitation solution, calibrator solution and/or control solutions. Optionally, microtitre plates or test tubes of the type which can be evaluated in standardised laboratory apparatus may optionally be included in the test kit, as well as instructions for use.

The zero control solution included in the test kit contains water or saliva imitation solution. The zero control solution must result in an extinction of 0. The positive control comprises water or saliva imitation solution with dye or saliva-collecting solution. The positive control must result in an extinction greater than 0.

Figure 2:
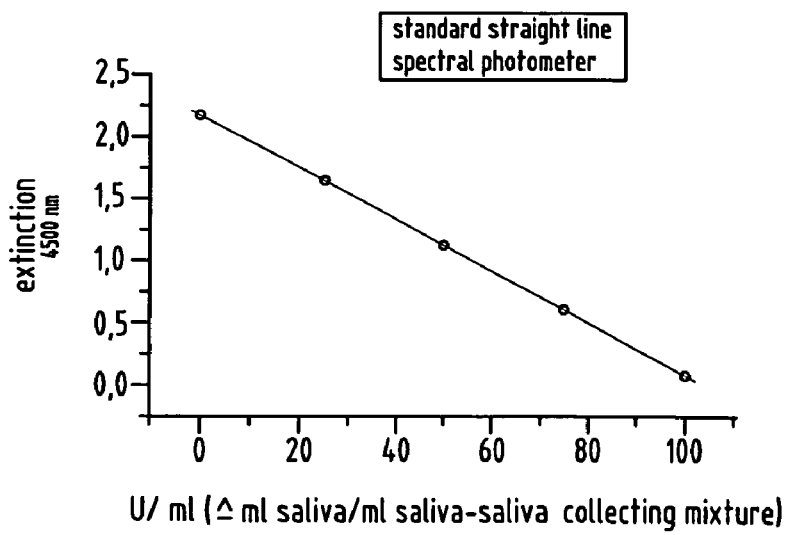
FIG. 2 illustrates the results of a quantification of the saliva volume plotted by a standard straight line determined with a spectral photometer.

FIG. 2 illustrates a standard straight line plotted using a spectral photometer for calibrator solutions 1 to 5, whereby in each case 1 ml of the calibration solutions 1 to 5 are pipetted into 1 cm test tubes and measured at a wavelength of 450 nm in a standard spectral photometer. Plotted on the X axis is the percentage of the saliva volume corresponding to the units of dye/ml of saliva-saliva collecting solution mixture, per milliliter of sample whilst the Y axis sets the extinction at a wavelength of 450 nm.

Taking a comparative measurement of the optical density of the saliva-saliva collecting solution mixture from the evacuated collection vessel at a wavelength of 450 nm for comparison with the calibrator solutions 1 to 5 then enables the volume of saliva per ml of sample to be determined.

When determining the test substances, in particular on a quantitative basis, the saliva from the supernatant of the evacuated collection vessel can therefore be used to make allowance for the quantity of saliva originally taken.

Amongst other things, the saliva-collecting solution is used to stimulate the saliva flow and, like the calibrator solution and the test kit, as a means of quantifying the saliva volume.

The container (1) is used to collect biological fluids, in particular saliva or saliva-saliva collecting solution mixture and transferring it into a sealable collection vessel.

The sealable collection vessel is used for centrifugation and analysing the sample contained in it, in particular the supernatant.

The saliva imitation solution is used to make up control and/or calibrator solutions.

Naturally, the invention lends itself not only to human medicine but also to veterinary medicine, given a few slight modifications, such as using the albumin of the saliva imitation solution corresponding to the particular animal species, for example.

The method of collecting saliva and the test kit and components contained in it can also be used for home care.

Embodiment 1

Before gargling 2 ml of saliva-collecting solution corresponding to the composition listed in the table, the patient rinses the mouth with distilled water in order to remove any food remains or other components which might lead to distortion from the oral cavity.

Saliva-Collecting Solution:

| Pilocarpin | 6 mg |
| --- | --- |
| Yellow orange S | 200 mg |
| Cholesterine | 100 mg |
| Strawberry flavouring | 10 mg |
| Top up with distilled water to a volume of 1000 ml | |
| Adjust to a pH value of 4.5 | |

After gargling four times a minute, each time with 2 ml of saliva-collecting solution, all of the saliva-saliva collecting solution mixture in the container 1 is collected, the distance of the tubular projection 9 from the base of the base part 2 of the container 1 being 2 mm. A filtration unit 13 of glass wool is also disposed in the container 1, in the region of the tubular projection 9. The pore size of the filtration unit 13 is 50 μm.

The saliva-saliva collecting solution mixture is transferred to an evacuated collection vessel, which is coated with the solution specified in the table.

Solution with Reagents:

| | |
|---|---|
| Sodium azide | 0.01 g/l |
| Potassium chloride | 0.015 g/l |
| Sodium chloride | 3 g/l |

The collection vessel with the saliva-saliva collecting solution mixture contained in it is vortexed and centrifuged at 2,000 g for 30 minutes at 4° C. The pellet is discarded and the optical density of the supernatant is determined at a wavelength of 480 nm in a plate photometer, in which case 250 µl of the saliva-saliva collecting solution mixture is pipetted respectively into a well of a microtitre plate.

To enable quantification, the optical density of calibrator solutions 1 to 3 based on the composition set out in the table below are measured in parallel, likewise at a wavelength of 480 nm.

Calibrator Solutions:

| | Calibrator solution 1 | Calibrator solution 2 | Calibrator solution 3 | Calibrator solution 4 |
|---|---|---|---|---|
| Saliva-collecting solution | 99.5% | 66.65% | 33.3% | 0% |
| Saliva-imitating solution | 0% | 33.3% | 66.65% | 99.5% |
| Potassium benzoate | 0.5% | 0.5% | 0.5% | 0.5% |

The saliva-collecting solution used to make up the calibrator solution is based on the composition specified in the example given as embodiment 1 and the saliva imitation solution is based on the composition specified in the table below.

Saliva Imitation Solution:

| | |
|---|---|
| NaHCO$_3$ | 0.4 g |
| NaCl | 0.04 g |
| K$_2$CO$_3$ | 0.01 g |
| Human serum albumin | 20 mg |
| Urea | 10 mg |
| Top up with distilled water to 1000 ml | |
| Adjust to a pH value of 7.5 | |

For the purpose of the photometric measurement, the positive control is a solution 1 with a concentration of 10 U/ml, corresponding to a concentration of 10%, i.e. 0.1 ml saliva/ml sample, and a solution 2 with a concentration of 90 U/ml, corresponding to a concentration of 90%, i.e. 0.9 ml saliva/ml sample. The saliva volume determined is 10 ml.

Embodiment 2

The patient gargles 6 ml of saliva-collecting solution based on the composition specified in the table.

Saliva-Collecting Solution:

| | |
|---|---|
| Ascorbic acid | 4 g |
| Curcumin | 2 g |
| Top up with distilled water to a volume of 1000 ml | |
| Adjust to a pH value of 5 | |

After gargling the saliva-collecting solution for 5 minutes, the saliva-saliva collecting solution mixture is collected in the container 1, the distance of the tubular projection 9 from the base of the base part 2 of the container 1 being 0.9 mm. Also disposed in the container 1 in the region of the tubular projection 9 is a filtration unit 13 in the form of a nitrocellulose membrane between the penetration device 8 and the tubular projection 9. The pore size of the filtration unit 13 is 10 µm.

The saliva-saliva collecting solution mixture is transferred to an evacuated collection vessel, which is coated with the solution specified in the table.

Solution with Reagents:

| | |
|---|---|
| Potassium benzoate | 8 g/l |
| Sodium chloride | 15 g/l |

The collection vessel with the saliva-saliva collecting solution mixture contained in it is shaken and centrifuged at 1,500 g for 1 hour at room temperature. The pellet is discarded and the optical density of the supernatant is determined in a photometer at a wavelength of 400 nm.

To enable quantification, the optical density of calibrator solutions 1 to 11 is measured in parallel with the composition specified in the table, likewise at a wavelength of 400 nm.

Calibrator Solutions:

| | Calibrator solution 1 | Calibrator solution 2 | Calibrator solution 3 | Calibrator solution 4 | Calibrator solution 5 |
|---|---|---|---|---|---|
| Saliva-collecting solution | 99.95% | 89.95% | 79.95% | 69.95% | 59.95% |
| Saliva-imitating solution | 0% | 10% | 20% | 30% | 40% |
| Thimerosal ® | 0.05% | 0.05% | 0.05% | 0.05% | 0.05% |

| | Calibrator solution 6 | Calibrator solution 7 | Calibrator solution 8 | Calibrator solution 9 | Calibrator solution 10 | Calibrator solution 11 |
|---|---|---|---|---|---|---|
| Saliva-collecting solution | 49.975% | 40% | 30% | 20% | 10% | 0% |
| Saliva-imitating solution | 49.975% | 59.95% | 69.95% | 79.95% | 89.95% | 99.95% |
| Thimerosal ® | 0.05% | 0.05% | 0.05% | 0.05% | 0.05% | 0.05% |

The saliva-collecting solution used to make up the calibrator solution is based on the composition specified in the example given as embodiment 2 and the saliva imitation solution is based on the composition specified in the table below.

Saliva Imitation Solution:

| | |
|---|---|
| NaHCO$_3$ | 0.002 g |
| NaCl | 0.03 g |
| K$_2$CO$_3$ | 0.08 g |
| Human serum albumin | 50 mg |
| Urea | 50 mg |
| Lactoferrin | 0.01 mg |
| Gelatine | 100 mg |
| Top up with distilled water to 1000 ml | |
| Adjust pH value to 6.8 | |

For the photometric measurement, the positive control is a solution with 50 U/ml, which corresponds to a saliva concentration per ml sample of 50%, i.e. 0.5 ml saliva/ml sample. The saliva volume taken in this embodiment of the experiment is 2 ml.

Embodiment 3

Before gargling 5 ml saliva-collecting solution based on the composition specified in the table, the patient rinses the mouth with distilled water in order to remove any food remains or other components which might cause distortion from the oral cavity.

Saliva-Collecting Solution:

| | |
|---|---|
| Sodium dihydrogen citrate | 20 g |
| Sodium citrate tribasic monocitrate | 8 g |
| Glucose | 5 g |
| Top up with distilled water to a volume of 1000 ml | |
| Adjust pH value to 4.0 | |

After gargling with the saliva-collecting solution for three minutes, the saliva-saliva collecting solution mixture is collected in the container 1, the distance of the tubular projection 9 from the base of the base part 2 of the container 1 being 3 millimeters.

The saliva-saliva collecting solution mixture is transferred to an evacuated collection vessel, which is coated with the solution specified in the table.

Solution with Reagents:

| | |
|---|---|
| Potassium benzoate | 1 g/l |
| Potassium chloride | 0.05 g/l |

The collection vessel with the saliva-saliva collecting solution mixture contained in it is tilted and centrifuged at 2,500 g for 3 minutes at room temperature. The pellet is discarded and the optical density of the supernatant is measured in a spectral photometer at a wavelength of 380 nm.

To enable quantification, the optical density of calibrator solutions 1 to 5 based on the compositions set out in the table below is measured in parallel, likewise at a wavelength of 450 nm.

Calibrator Solutions:

| | Calibrator solution 1 | Calibrator solution 2 | Calibrator solution 3 | Calibrator solution 4 | Calibrator solution 5 |
|---|---|---|---|---|---|
| Saliva-collecting solution | 99.95% | 69.95% | 39.95% | 20% | 0% |
| Saliva-imitating solution | 0% | 30% | 60% | 79.95% | 99.95% |
| Sodium azide | 0.05% | 0.05% | 0.05% | 0.05% | 0.05% |

The saliva-collecting solution used to make up the calibrator solution is based on the composition specified in the example given as embodiment 3 and the saliva imitation solution is based on the composition set out in the table below.

Saliva Imitation Solution:

| | |
|---|---|
| NaHCO$_3$ | 10 g |
| CaCl$_2$ | 1 g |
| K$_2$CO$_3$ | 0.1 g |
| Human serum albumin | 750 mg |
| Urea | 500 mg |
| Gelatine | 1 g |
| Top up with distilled water to 1000 ml | |
| Adjust pH value to 5.5 | |

For the enzymatic photometric test, calibrator solutions 2 and 4 are used as a positive control. The measured saliva volume is 6 ml.

Embodiment 4

Before gargling 3 ml of saliva-collecting solution based on the composition listed in the table, the patient rinses the mouth with distilled water in order to remove any food remains or other components which might cause distortion from the oral cavity.

Saliva-Collecting Solution:

| | |
|---|---|
| Sodium hydrogen citrate | 7 g |
| Sodium citrate tribasic monocitrate | 2 g |
| Tartrazine | 50 mg |
| Top up with distilled water to a volume of 1000 ml | |
| Adjust to a pH value of 4.2 | |

After gargling with the saliva-collecting solution for one minute, the saliva-saliva collecting solution mixture is collected in the container 1, the distance of the tubular projection 9 from the base of the base part 2 of the container 1 being one millimeter. Also disposed in the container 1 in the region of the tubular projection 9 is a filtration unit 13 of cellulose triacetate. The pore size of the filtration unit 13 is 30 μm.

The saliva-saliva collecting solution mixture is transferred to an evacuated collection vessel, which is coated with the solution specified in the table.

Solution with Reagents:

| | |
|---|---|
| Sodium azide | 0.5 g/l |
| Ammonium sulphate | 1.5 g/l |

The collection vessel with the saliva-saliva collecting solution mixture contained in it is tilted and centrifuged at 1,800 g for 10 minutes at room temperature. The pellet is discarded and the extinction of the supernatant is measured in a spectral photometer at a wavelength of 450 nm.

To enable quantification, the extinction of calibrator solutions 1 to 5 based on the composition specified in the table below is measured in parallel, likewise at a wavelength of 450 nm.

Calibrator Solutions:

|  | Calibrator solution 1 | Calibrator solution 2 | Calibrator solution 3 | Calibrator solution 4 | Calibrator solution 5 |
|---|---|---|---|---|---|
| Saliva-collecting solution | 99.95% | 74.95% | 49.975% | 25% | 0% |
| Saliva-imitating solution | 0% | 25% | 49.975% | 74.95% | 99.95% |
| Sodium azide | 0.05% | 0.05% | 0.05% | 0.05% | 0.05% |

The saliva-collecting solution used to make up the calibrator solution is based on the composition specified in the example given as embodiment 4 and the saliva imitation solution is based on the composition specified in the table below.

Saliva Imitation Solution:

| | |
|---|---|
| $NaHCO_3$ | 4.2 g |
| NaCl | 0.5 g |
| $K_2CO_3$ | 0.2 g |
| Human serum albumin | 250 mg |
| Urea | 150 mg |
| Lactoferrin | 0.1 mg |
| Gelatine | 500 mg |
| Top with distilled water to 1000 ml | |
| Adjust to pH value of 6.5 | |

Two controls are used for the photometric measurement. Control 1 has a concentration of 20 U/ml (%) and control 2 of 60 U/ml (%), in which case 1 U/ml (%) corresponds to 0.01 ml saliva in the saliva-collecting solution. The saliva volume taken is 3 ml.

Embodiment 5

Before gargling at least four times, each time with 1.5 ml of saliva-collecting solution based on the composition set out in the table, the patient rinses the mouth with distilled water in order to remove any food remains or other components which might cause distortion from the oral cavity.

Saliva-Collecting Solution:

| | |
|---|---|
| Sodium dihydrogen citrate | 12 g |
| Sodium citrate tribasic monocitrate | 6 g |
| Tartrazine | 30 mg |
| Top up with distilled water to a volume of 1000 ml | |
| Adjust to a pH value of 5.2 | |

After gargling the saliva-collecting solution, each time for one minute, the saliva-saliva collecting solution mixture is collected in the container 1, the distance of the tubular projection 9 form the base of the base part 2 of the container 1 being 2 mm. Also disposed in the container 1 in the region of the tubular projection 9 is a filtration unit 13 of cotton wall. The pore size of the filtration unit 13 is 70 μm.

The saliva-saliva collecting solution mixture is transferred to an evacuated collection vessel, which is coated with the solution specified in the table.

Solution with Reagents:

| | |
|---|---|
| Thimerosal ® | 0.05 g/l |
| Ammonium sulphate | 0.5 g/l |

The collection vessel with the saliva-saliva collecting solution mixture contained in it is tilted and centrifuged at 1,500 g for 20 minutes at 4° C. The pellet is discarded and the optical density of the supernatant is measured in a spectral photometer at a wavelength of 420 nm.

To enable a quantification, the optical density of calibrator solutions 1 to 5 based on the composition specified in the table below is measured in parallel, likewise at a wavelength of 420 nm.

Calibrator Solutions:

|  | Calibrator solution 1 | Calibrator solution 2 | Calibrator solution 3 |
|---|---|---|---|
| Saliva-collecting solution | 99.95% | 49.975% | 0% |
| Saliva-imitating solution | 0% | 49.975% | 99.95% |
| Sodium azide | 0.05% | 0.05% | 0.05% |

The saliva-collecting solution used to make up the calibrator solution is based on the composition specified in the example given as embodiment 5 and the saliva imitation solution is based on the composition specified in the table below.

Saliva Imitation Solution:

| | |
|---|---|
| $NaHCO_3$ | 2 g |
| NaCl | 5 g |
| $K_2CO_3$ | 2 g |
| Human serum albumin | 2 g |
| Urea | 1 g |
| Lactoferrin | 1 mg |
| Top up with distilled water to 1000 ml | |
| Adjust to a pH value of 7 | |

As a negative control for the photometric measurement, the saliva imitation solution specified in the table above is used and calibration solution 1 is used as a positive control. The saliva volume taken is 7 ml.

Embodiment 6

Before gargling 2 ml of saliva-collecting solution based on the composition specified in the table, the patient rinses the mouth with distilled water in order to remove any food remains or other component which might cause distortion from the oral cavity.

Saliva-Collecting Solution:

| | |
|---|---|
| Sodium dihydrogen citrate | 1 g |
| Sodium citrate tribasic monocitrate | 0.2 g |
| Testosterone | 10 ng |
| Top up with distilled water to a volume of 1000 ml | |
| Adjust to a pH value of 4.2 | |

After gargling for one minute with the saliva-collecting solution, the saliva-saliva collecting solution mixture is collected in the container 1, the distance of the tubular projection 9 from the base of the base part 2 of the container 1 being 2 mm. Also disposed in the container 1 in the region of the tubular projection 9 is a filtration unit 13 of nitrocellulose. The pore size of the filtration unit 13 is 40 μm.

The saliva-saliva collecting solution mixture is transferred into an evacuated collection vessel, which is coated with the solution specified in the table.

Solution with Reagents:

| | |
|---|---|
| Potassium sorbate | 0.5 g/l |
| Potassium chloride | 1.5 g/l |

The collection vessel with the saliva-saliva collecting solution mixture contained in it is tilted and centrifuged at 1,600 g for 8 minutes at room temperature. The pellet is discarded and testosterone in the supernatant is immunologically determined by means of Elisa. The concentration of testosterone prior to rinsing the oral cavity with saliva-collecting solution is also determined from the saliva in order to make allowance for the presence of physiological testosterone. This means that no testosterone is detected in the saliva prior to starting the method proposed by the invention.

To enable a quantification, the testosterone concentration of calibrator solutions 1 to 5 based on the composition specified in the table below is also measured in parallel by means of Elisa.

Calibrator Solutions:

| | Calibrator solution 1 | Calibrator solution 2 | Calibrator solution 3 | Calibrator solution 4 | Calibrator solution 5 |
|---|---|---|---|---|---|
| Saliva-collecting solution | 99.95% | 74.95% | 49.975% | 25% | 0% |
| Saliva-imitating solution | 0% | 25% | 49.975% | 74.95% | 99.95% |
| Sodium azide | 0.05% | 0.05% | 0.05% | 0.05% | 0.05% |

The saliva-collecting solution used to make up the calibrator solution is based on the composition specified in the example given as embodiment 6 and the saliva imitation solution is based on the composition specified in the table below.

Saliva Imitation Solution:

| | |
|---|---|
| $NaHCO_3$ | 4.2 g |
| NaCl | 0.5 g |
| $K_2CO_3$ | 0.2 g |
| Human serum albumin | 250 mg |
| Urea | 150 mg |
| Lactoferrin | 0.1 mg |
| Gelatine | 500 mg |
| Top up with distilled water to 1000 ml | |
| Adjust pH value to 6.5 | |

Two controls are used for immunological detection. Control 1 has a concentration of 20 ng/ml and control 2 of 60 ng/ml. The saliva volume taken is 3 ml.

Embodiment 7

Before gargling 3 ml of saliva-collecting solution based on the composition specified in the table, the patient rinses the mouth with distilled water in order to remove any food remains or other components which might cause distortion from the oral cavity.

Saliva-Collecting Solution:

| | |
|---|---|
| Sodium dihydrogen citrate | 7 g |
| Sodium citrate tribasic monocitrate | 2 g |
| Vitamin B9 | 5 μg |
| Top up with distilled water to a volume of 1000 ml | |
| Adjust pH value to 4.2 | |

After gargling the saliva-collecting solution for one minute, the saliva-saliva collecting solution mixture is collected in the container 1, the distance of the tubular projection 9 from the base of the base part 2 of the container 2 being one millimeter. Also disposed in the container 1 in the region of the tubular projection 9 is a filtration unit 13 of cellulose triacetate. The pore size of the filtration unit 13 is 80 μm.

The saliva-saliva collecting solution mixture is transferred to an evacuated collection vessel, which is coated with the solution specified in the table.

Solution with Reagents:

| | |
|---|---|
| Potassium benzoate | 0.5 g/l |
| Ammonium sulphate | 1.5 g/l |

The collection vessel with the saliva-saliva collecting solution mixture contained in it is tilted and centrifuged at 1,500 g for 15 minutes at room temperature. The pellet is discarded and the supernatant is transferred to a HPLC and the concentration determined by means of the software installed in the apparatus.

To enable a quantification, calibrator solutions 1 to 5 based on the composition specified in the table below are measured, likewise in the HPLC.

Calibrator Solutions:

| | Calibrator solution 1 | Calibrator solution 2 | Calibrator solution 3 | Calibrator solution 4 | Calibrator solution 5 |
|---|---|---|---|---|---|
| Saliva-collecting solution | 99.95% | 74.95% | 49.975% | 25% | 0% |
| Saliva-imitating solution | 0% | 25% | 49.975% | 74.95% | 99.95% |
| Sodium azide | 0.05% | 0.05% | 0.05% | 0.05% | 0.05% |

The saliva-collecting solution used to make up the calibrator solution is based on the composition specified in the example given as embodiment 7 and the saliva imitation solution is based on the composition specified in the table below.

Saliva Imitation Solution:

| | |
|---|---|
| NaHCO$_3$ | 2.2 g |
| CaCl$_2$ | 1 g |
| K$_2$CO$_3$ | 0.02 g |
| Human serum albumin | 250 mg |
| Urea | 150 mg |
| Gelatine | 500 mg |
| Top up with distilled water to 1000 ml | |
| Adjust pH value to 5.5 | |

For the HPLC detection, positive controls are also determined in accordance with the manufacturer's instructions for the apparatus.

The examples of embodiments given above describe possible variants of the method for collecting saliva, the saliva-collecting solution, the container, the sealable collection vessel, the saliva imitation solution, the calibrator solutions and the test kit, although it should be pointed out at this stage that the invention is not restricted to the specific variants of them described here and instead, various different combinations of the individual variants are possible and these and the ability to make these variations is within the ability of the person skilled in this technical field with the aid of the technical teaching relating to the subject matter of the invention. Accordingly, all conceivable variants which can be obtained by combining individual details of the illustrated and described variants are also possible and fall within the scope of the invention.

For the sake of good order, it should be pointed out that in order to provide a clearer illustration of the structure of the container, it and its constituent parts are illustrated to a certain extent out of scale and/or on an enlarged scale and/or on a reduced scale.

The independent solutions proposed by the invention and the underlying objectives may be found in the description.

LIST OF REFERENCE NUMBERS

1 Container
2 Base part
3 Cover part
4 Internal face
5 External face
6 Cut-out
7 Transfer mechanism
8 Penetration device
9 Projection
10 End
11 End
12 Distance
13 Filtration unit

The invention claimed is:

1. A method of collecting and quantifying a sample of saliva from the oral cavity in order to detect a test substance, comprising the steps of
(a) cleaning the oral cavity,
(b) stimulating saliva secretion with a saliva-collecting solution, said saliva collecting solution comprising an aqueous solution comprising
a substance with taste-stimulating properties, which stimulates saliva secretion, in a range of 0.0005% by weight per volume lower limit up to 10% by weight per volume upper limit;
an indicator substance, tartrazine in concentration in a range of 0.0001% by weight per volume lower limit up to 5% by weight per volume upper limit to indicate the ratio of saliva saliva-collection solution; and
said saliva-collection solution having an optical density at a wavelength of 450 nm within a range of 1.5 up to 2.6;
(c) removing the saliva-saliva collecting solution mixture from the oral cavity and collecting it in a container (1) in FIG. 1, and
(d) transferring the saliva-saliva collecting solution mixture to a sealable, optionally evacuated, collection vessel,
(e) measuring optical density of the collected solution and comparing with the measurement of control solution, wherein the difference in measurement indicates the presence of the test substance.

2. Method according to claim 1, wherein the secretion of saliva is increased by the substance with taste-stimulating properties selected from the group of inorganic and/or organic edible acids such as phosphoric acid, lactic acid, citric acid, ascorbic acid and/or salts or mixtures thereof and/or an active substance such as pilocarpin.

3. Method according to claim 1, wherein the saliva-saliva collecting solution mixture is transferred via a transfer mechanism (7) integrated in or on the container (1) into the sealable collection vessel in FIG. 1.

4. Method according to claim 1, wherein particulate elements of the oral cavity are removed from the saliva-saliva collecting solution mixture by means of a filtration unit (13) in the container (1) in FIG. 1.

5. Method according to claim 1, wherein the sealable collection vessel is used with a solution having preserving and reducing properties.

6. Method according to claim 1, wherein the quantity of saliva is quantitatively determined.

7. Method according to claim 1, wherein the saliva is quantified using at least one calibrator solution.

8. Method according to claim 1, wherein in order to make a quantitative determination, the concentration and/or extinction of the indicator substance and/or reagent of the saliva-saliva collecting solution mixture is compared with the concentration and/or extinction of the indicator substance and/or reagent present in the saliva prior to taking the sample.

9. Method according to claim 1, wherein the saliva-saliva collecting solution mixture present in the evacuated collection vessel is centrifuged and optionally mixed beforehand.

10. Method according to claim 1, wherein the saliva-saliva collecting solution mixture is used for conducting tests.

11. Method according to claim 1, wherein the tests are conducted in standardised laboratory measuring equipment.

12. A method of collecting and quantifying a sample of saliva from the oral cavity in order to detect a test substance, comprising the steps of
(a) cleaning the oral cavity,
(b) stimulating saliva secretion with a saliva-collecting solution, said saliva collecting solution comprising
an aqueous solution comprising
a substance with taste-stimulating properties, which stimulates saliva secretion, in a range of 0.0005% by weight per volume lower limit up to 10% by weight per volume upper limit;
an indicator substance, tartrazine in concentration in a range of 0.0001% by weight per volume lower limit up to 5% by weight per volume upper limit to indicate the ratio of saliva saliva-collection solution; and said saliva-collection solution having an optical density at a wavelength of 450 nm within a range of 1.5 up to 2.6, and having an pH from 5.0 to 6.0;

(c) removing the saliva-saliva collecting solution mixture from the oral cavity and collecting it in a container (1) in FIG. 1, and (d) transferring the saliva-saliva collecting solution mixture to a sealable, optionally evacuated, collection vessel, (e) measuring optical density of the collected solution and comparing with the measurement of control solution, wherein the difference in measurement indicates the presence of the test substance.

\* \* \* \* \*